US005786223A

United States Patent [19]

Terashima et al.

[11] Patent Number: 5,786,223
[45] Date of Patent: Jul. 28, 1998

[54] TWO-STEP CALIBRATION METHOD FOR DRY CHEMICAL ANALYSIS ELEMENT

[75] Inventors: Kaoru Terashima; Osamu Seshimoto, both of Saitama-ken, Japan

[73] Assignee: Fuji Photo Film Co., Ltd., Kanagawa, Japan

[21] Appl. No.: 650,877

[22] Filed: May 17, 1996

[30] Foreign Application Priority Data

| May 19, 1995 | [JP] | Japan | 7-121248 |
| Apr. 30, 1996 | [JP] | Japan | 8-109401 |

[51] Int. Cl.$^6$ .................................................... G01N 37/00
[52] U.S. Cl. ................................. 436/50; 436/43; 436/46; 428/63; 428/67
[58] Field of Search ............................ 422/63, 64, 67; 436/43, 50, 55; 364/497, 498

[56] References Cited

U.S. PATENT DOCUMENTS

| 4,043,756 | 8/1977 | Sommervold | 422/67 |
| 4,884,213 | 11/1989 | Iwata et al. | 364/497 |
| 5,424,212 | 6/1995 | Pinsl-Ober et al. | 436/50 |
| 5,550,053 | 8/1996 | Salpeter | 436/8 |
| 5,583,049 | 12/1996 | Altman et al. | 436/55 |

Primary Examiner—Long V. Le
Attorney, Agent, or Firm—McAulay Fisher Nissen Goldberg & Kiel, LLP

[57] ABSTRACT

The concentration of an analyte in a sample liquid is determined on the basis of the optical density of a chemical analysis element spotted with the sample liquid according to a standard curve representing the relation between the concentration and the optical density of the analysis element which is obtained when the concentration is measured using an analysis element of a first lot. A plurality of first standard liquids containing the analyte in known levels are spotted onto analysis elements of a second lot, the concentrations of the analyte in the first standard liquids are determined according to the standard curve and a first calibration curve for correcting the concentrations of the analyte is prepared. A plurality of second standard liquids containing the analyte in known levels are spotted onto analysis elements of the second lot, the concentrations of the analyte in the second standard liquids are determined according to the standard curve on the particular analysis system, the concentrations of the analyte in the second standard liquids thus determined are corrected according to the first calibration curve, and a second calibration curve for correcting the concentrations of the specific analyte in the second standard liquids thus corrected is prepared.

5 Claims, 4 Drawing Sheets

TWO-STEP CALIBRATION METHOD FOR DRY CHEMICAL ANALYSIS ELEMENT

BACKGROUND OF THE INVENTION

1. Field of the Invention

This invention relates to a method of calibrating a concentration (or activity) of a biochemical substance in quantitative analysis of a biochemical substance contained in sample liquid such as blood, urine or the like in which the concentration of the biochemical substance is determined by colorimetry using a dry chemical analysis element. That is, in quantitative analysis of a biochemical substance contained in sample liquid, the sample liquid is spotted onto a dry chemical analysis element and the concentration of the biochemical substance is determined on the basis of the optical density of the chemical analysis element spotted with the sample liquid according to a standard curve representing the relation of the optical density of the chemical analysis element and the concentration of the biochemical substance. This invention relates to a method of calibrating the concentration of the biochemical substance thus determined and more particularly to such a method in which the concentration of the biochemical substance is calibrated in two steps.

2. Description of the Related Art

Quantitative or qualitative analysis of a specific chemical component in a sample liquid is a common operation carried out various industrial fields. Especially quantitative analysis of a chemical component or a solid component contained in body fluid such as blood or urine is very important in the filed of clinical biochemistry.

Recently there has been put into practice a dry ("dry-to-the-touch") chemical analysis film with which a specific chemical component or a specific solid component contained in a sample liquid can be quantitatively analyzed through a droplet of the sample liquid. See, for instance, Japanese Patent Publication No. 53(1978)-21677 (U.S. Pat. No. 3,992,158), Japanese Unexamined Patent Publication No. 55(1980)-164356 (U.S. Pat. No. 4,292,272). When such a dry chemical analysis film is used, the sample liquid can be quantitatively analyzed more easily and more quickly than when the conventional wet analysis method is used, and accordingly the dry chemical analysis film is very convenient for medical facilities, laboratories and the like where lots of sample liquids have to be analyzed.

As such a dry chemical analysis film, there has been known an integrated multi-layered chemical analysis film comprising a support sheet of organic polymer or the like and at least one reagent layer formed on the support sheet. A spreading layer is sometimes provided on the reagent layer.

Such dry chemical analysis films are generally in the form of a film chip of a predetermined shape such as rectangle or square. The film chip is sometimes provided with a frame of organic polymer or the like for flattening the film chip in order to facilitate automated handling of the chemical analysis film and sometimes used as it is without frame. The former is generally referred to as "a chemical analysis slide" and the latter is generally referred to as "a frameless chemical analysis film". Further a dry chemical analysis element which is formed of filter paper and has one or more layers has been proposed, for instance, in U.S. Pat. No. 4,477,575 and partly put into practice. In this specification, the term "chemical analysis element" should be broadly interpreted to include the chemical analysis slide, the frameless chemical analysis film and the single-layered or multi-layered chemical analysis element formed of filter paper (with or without frame).

For instance, blood sugar (glucose), cholesterol, urea nitrogen (BUN), creatinine, bilirubin, hemoglobin, GOT (glutamic oxaloacetic transaminase) or AST (asparate aminotransferase), GPT (glutamic pyruvic transaminase) or ALT (alanine aminotransferase), amylase and C-reactive protein can be quantitatively analyzed by use of the dry chemical analysis element.

When quantitatively analyzing a chemical component, biochemical component, immunological component or the like contained in a sample liquid using such a dry chemical analysis element, a droplet of the sample liquid is spotted onto the chemical analysis element and is held at a constant temperature for a predetermined time (incubation) in an incubator so that coloring reaction occurs, and the optical density of the color formed by the coloring reaction is optically measured. That is, measuring light containing a wavelength which is pre-selected according to the combination of the component to be analyzed and the reagent contained in the reagent layer of the chemical analysis element is projected onto the chemical analysis element and the reflective optical density of the chemical analysis element is measured. Then the concentration or the activity of the component to be analyzed is determined on the basis of the reflective optical density using a standard curve which represents the relation between the concentration (to be broadly interpreted to include both the concentration and the activity) of the component and the reflective optical density of the chemical analysis element.

When the concentration of a specific substance in a solution is measured, a transmitting optical density is generally used, and such a measurement is carried out in a range of the concentration of the solution where the transmitting optical density and the concentration of the specific substance are linearly related to each other. Accordingly a standard curve can be easily prepared by use of two calibrators (standard liquids) having different levels, and so the standard curve is prepared for each measurement.

On the other hand, when a biochemical substance in a sample liquid is analyzed using a dry chemical analysis element, the optical density of light reflected at the chemical analysis element is measured and the concentration of the biochemical substance is determined on the basis of the optical density. However since the reflective optical density and the concentration of the substance are not linearly related with each other, it takes a long time to prepare the standard curve and accordingly preparing the standard curve for each measurement elongates the time required for analysis. Accordingly when a biochemical substance in a sample liquid is analyzed using a chemical analysis element, a reference production lot is selected out of a number of production lots, and a basic standard curve is prepared using the chemical analysis elements produced in the reference production lot and standard sample liquids containing therein a specific biochemical substance in known concentrations. The basic standard curve thus prepared is stored in a memory in a biochemical analysis system as a built-in standard curve and the concentration of the specific biochemical component to be analyzed (will be referred to as "analyte", hereinbelow) is determined according to the built-in standard curve.

However since the properties and the performance of the chemical analysis elements are apt to slightly differ from production lot to production lot even if they are produced under the same condition, the measured value fluctuates by production lot of the chemical analysis element used when the concentration of the analyte is determined solely on the built-in standard curve. Depending on the accuracy requirement, such a small fluctuation in the measured value gives rise to a problem.

In order to overcome such a problem, there has been proposed a technique in Japanese Unexamined Patent Publication No. 05(1993)-264535 (EP 0 562 425A).

In the technique, standard liquids of a plurality of levels (normally three to four levels) are spotted onto chemical analysis elements of each production lot, five to ten chemical analysis elements for each level, and the concentration of an analyte in each standard liquid is measured for each chemical analysis element spotted with each standard liquid. Then a correction value is determined for each production lot of the chemical analysis elements so that the difference in measured value between the production lots is nullified and the correction value is recorded on a recording medium such as a magnetic card. These steps are carried out by the maker of the chemical analysis element. The user inputs the correction value recorded on the recording medium into the biochemical analysis system and the system corrects the built-in standard curve on the basis of the correction value and determines the concentration of the analyte according to the corrected standard curve.

However when one or two years lapses after production of the chemical analysis element before the user actually uses the chemical analysis element, the reagent layer of the chemical analysis element changes with time to some extent, which results in difference in the measured value from that measured by use of a chemical analysis element just produced.

Further the measured value can fluctuate by the biochemical analysis system used.

Accordingly there has been a demand for a technique of biochemical analysis which can effect biochemical analysis with a higher accuracy free from fluctuation in measured value.

SUMMARY OF THE INVENTION

In view of the foregoing observations and description, the primary object of the present invention is to provide a method of calibrating the measured concentration of analyte measured by use of a chemical analysis element which can prevent fluctuation in the measured concentration due to difference of the chemical analysis element between production lots, due to change with time of the chemical analysis element, or due to difference in properties between the biochemical analysis systems used.

In accordance with the present invention, there is first prepared a standard curve which represents the relation between the concentration of a specific analyte in a sample liquid and the optical density of the chemical analysis element spotted with the sample liquid (or other physical value corresponding to the optical density) which is obtained when the concentration of the specific analyte is measured using a chemical analysis element produced in a first production lot.

Then a plurality of first standard liquids containing therein said specific analyte in different levels (concentrations or activities) which are known are spotted onto like number of chemical analysis elements produced in a second production lot other than the first production lot, and the concentrations of the specific analyte in the respective first standard liquids are determined according to the standard curve. Then there is prepared a first calibration curve for correcting the values of the concentrations of the specific analyte in the respective first standard liquids thus determined to the values which would be obtained when the concentrations of the specific analyte in the respective first standard liquids are determined using chemical analysis elements produced in the first production lot and the standard curve.

Then, before quantitatively analyzing the specific analyte in a sample liquid using a chemical analysis element of said second production lot on a particular biochemical analysis system, a plurality of second standard liquids containing therein said specific analyte in different levels which are known are spotted onto like number of chemical analysis elements of the second production lot, and the concentrations of the specific analyte in the respective second standard liquids are determined according to the standard curve on said particular biochemical analysis system. The values of the concentrations of the specific analyte in the respective second standard liquids thus determined are corrected according to the first calibration curve.

Then there is prepared a second calibration curve for correcting the values of the concentrations of the specific analyte in the respective second standard liquids thus corrected to the values which would be obtained when the concentrations of the specific analyte in the respective standard liquids are determined using chemical analysis elements produced in the first production lot and the standard curve.

When fluctuation in the measured concentration due to change with time of the chemical analysis element and that depending on the biochemical analysis system used are negligible, the step of preparing the second calibration curve may be omitted.

When quantitatively analyzing the specific analyte in a sample liquid using a chemical analysis element of said second production lot on the particular biochemical analysis system, the value of the concentration of the specific analyte in the sample liquid as determined according to the standard curve is corrected in two steps. That is, the value of the concentration of the specific analyte in the sample liquid as determined according to the standard curve is first corrected according to the first calibration curve and the corrected value is further corrected according to the second calibration curve.

The first calibration curve is for compensating for fluctuation in the measured concentration due to difference of the chemical analysis element between production lots, and the second calibration curve is for compensating for fluctuation in the measured concentration due to change with time of the chemical analysis element and that depending on the biochemical analysis system used. Accordingly, in accordance with the present invention, even if the chemical analysis element used for analyzing the sample liquid is produced in a production lot other than that in which the chemical analysis element used for preparing the standard curve is produced and even if one or two years lapses after production of the chemical analysis element before the user actually uses the chemical analysis element and the biochemical analysis system used for analyzing the sample liquid greatly differs from that used for preparing the standard curve in the maker, the fluctuation in the measured value due to such factors can be compensated for and an accurate result of analysis can be obtained. Especially the measured value of the concentration of the specific analyte can be correctly compared with past values.

Since the first calibration curve is for compensating for fluctuation in the measured concentration due to difference of the chemical analysis element between production lots, standard liquids of a plurality of levels containing therein a specific analyte in different levels which are known are spotted onto chemical analysis elements of each production lot, five to ten chemical analysis elements for each level, and the concentration of the analyte in each standard liquid is measured for each chemical analysis element spotted with each standard liquid. Then a correction value is determined for each production lot of the chemical analysis elements. Since the first calibration curve is generally a quadric or a curve which can be substantially approximated to a quadric, at least three values are necessary to determine the coefficients of the curve and accordingly at least three standard liquids of different levels must be analyzed, since the step of preparing the first calibration curve is such a troublesome step, it is preferred that the step of preparing the first calibration curve be carried out by the maker in view of lightening load on the user and improvement of reliability of analysis.

Since the second calibration curve is for compensating for fluctuation in the measured concentration due to change with time of the chemical analysis element and that depending on the biochemical analysis systems used (including change with time of the biochemical analysis system), the step of preparing the second calibration curve is generally carried out by the user. However since this step has only to be effected for a production lot which is actually used, load on the user is not so heavy.

When the second calibration curve is linear, use of two standard liquids of different levels (may be one when the linear line passes through the origin) suffices, which further facilitates preparation of the second calibration curve.

When it is difficult to represent the second calibration curve as a linear line, analysis can be effected with a high accuracy without substantially increasing load on the user by preparing the second calibration curve using three standard liquids of different levels.

DESCRIPTION OF THE PREFERRED EMBODIMENT

Figure 2:
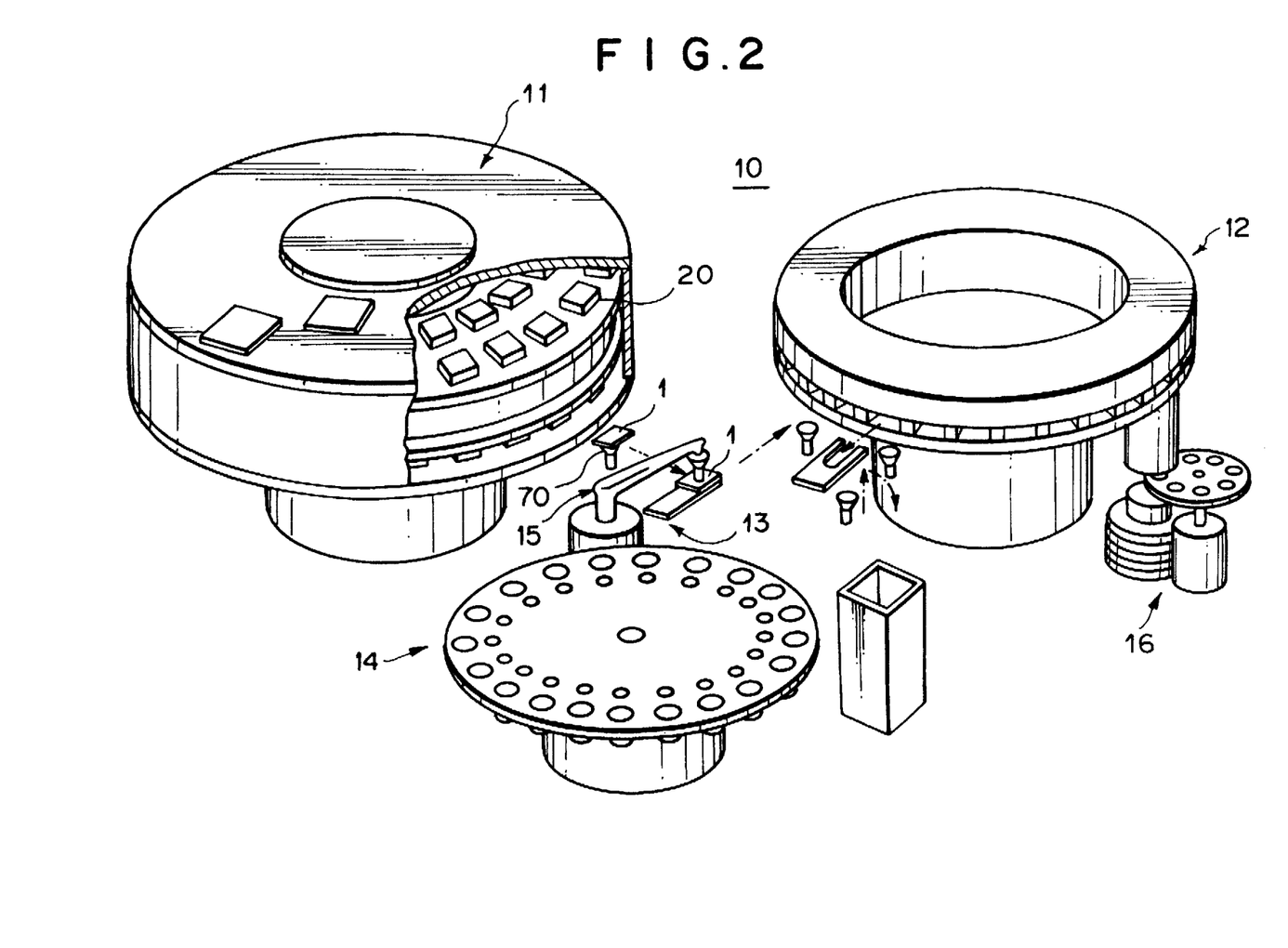
FIG. 2 is a schematic perspective view of a biochemical analysis system to which the method of the present invention is applied.

In FIG. 2, a biochemical analysis system 10 comprises a film supplier 11 in which a plurality of chemical analysis film cartridges 20 each containing a stack of a plurality of virgin dry frameless chemical analysis films 1 (which are rectangular or square in shape) are stored, an incubator 12 which is disposed beside the film supplier 11 and incubates the frameless chemical analysis films 1 spotted with sample liquids for a predetermined time at a constant temperature, a film transfer means 13 which transfers the frameless chemical analysis films 1 from the film supplier 11 to the incubator 12 with a suction pad 70, a sample liquid supplier 14 in which a plurality of sample liquids such as serum, urine and the like are stored, a spotting mechanism 15 which spots one of the sample liquids in the sample liquid supplier 14 onto the frameless chemical analysis film 1 on the way to the incubator 12, and an optical measuring system 16 disposed below the incubator 12.

The biochemical analysis system 10 is disclosed in detail, for instance, in Japanese Unexamined Patent Publication No. 7(1995)-35746 (EP 0 634 657A).

The frameless chemical analysis film 1 comprises a transparent support sheet formed of plastic or organic polymer such as polyethylene terephthalate, polystyrene or the like, a reagent layer and a spreading layer. That is, the frameless chemical analysis film 1 is formed by coating or bonding the reagent layer on the support sheet and laminating the spreading layer on the reagent layer.

The reagent layer comprises at least one layer composed of a hydrophilic polymer binder such as gelatin or a porous layer such as of filter paper, fabrics, porous polymer sheet containing therein a detecting reagent which selectively reacts with analyte and a reagent (chemical analysis reagent or immunoassay reagent) which is necessary for coloring reaction.

The spreading layer is formed of a material resistant to rubbing such as woven or knitted fabric (or cloth) of synthetic fiber such as polyester, or of blend of natural fiber and synthetic fiber, or paper, and functions as a protective layer. Further the spreading layer causes the sample liquid spotted onto the reagent layer to uniformly spread over the reagent layer.

As described above, the frameless chemical analysis film 1 spotted with a sample liquid is incubated in the incubator 12 and then the optical density of the frameless chemical analysis film 1 is measured by the optical measuring system 16 disposed below the incubator 12. The measuring system 16 has a light measuring head for measuring the optical density of dye formed by a coloring reaction between the reagent layer of the film 1 and the sample liquid. The light measuring head projects measuring light containing a predetermined wavelength onto the reagent layer through the transparent support sheet and detects reflected light from the reagent layer of the frameless chemical analysis film 1.

The reflected light from the reagent layer bearing thereon light information (i.e., the amount of light) according to the amount of dye formed in the reagent layer is received by a photodetector in the light measuring head and converted into an electric signal, which is input into a concentration determining section through an amplifier. The concentration determining section determines the amount of dye formed in the reagent layer on the basis of the level of the electric signal and executes an operation for determining the concentration of the specific analyte in the sample liquid using a standard curve which is a transform function of the optical density to the concentration of the specific analyte.

The standard curve is a curve which represents correspondence between the concentration of the specific analyte and the transmission optical density, the reflective optical density or other physical values such as an electric voltage corresponding to the optical density (the reflective density in this particular embodiment), and is prepared for each analyte by a maker of the frameless chemical analysis films using a predetermined biochemical analysis system and frameless chemical analysis films 1 produced in a reference production lot (may be any one of production lots and is referred to as "a first production lot" in claims) just after production of the frameless chemical analysis films 1. The standard curves for the respective analytes are stored in a memory in the concentration determining section.

Since the standard curve is prepared using a predetermined biochemical analysis system and frameless chemical analysis films 1 produced in a reference production lot, the result of measurement can deviate from that obtained by use of a frameless chemical analysis film 1 of the reference production lot when a user determines the concentration of the analyte according to the standard curve as it is. That is, the frameless chemical analysis films 1 used by the user are generally produced in a production lot different from the reference production lot (referred to as "a second production lot" in claims) and the biochemical analysis system used by the user generally differs from that used by the maker when preparing the standard curve. Further the frameless chemical analysis films 1 can change with time before the user actually uses them after production thereof. These factors can change the relation between the reflective optical density and the concentration of the analyte.

Figure 1:
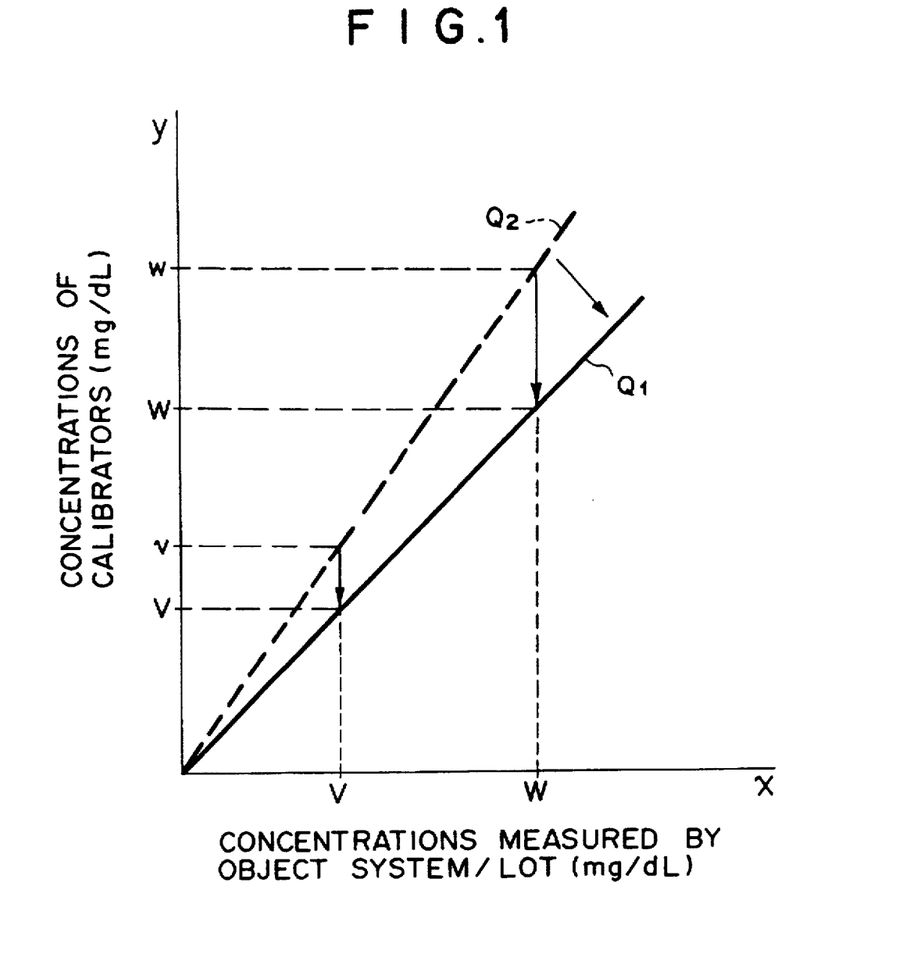
FIG. 1 is a graph for illustrating preparation of the second calibration curve in a method of calibration in accordance with an embodiment of the present invention.
Figure 3:
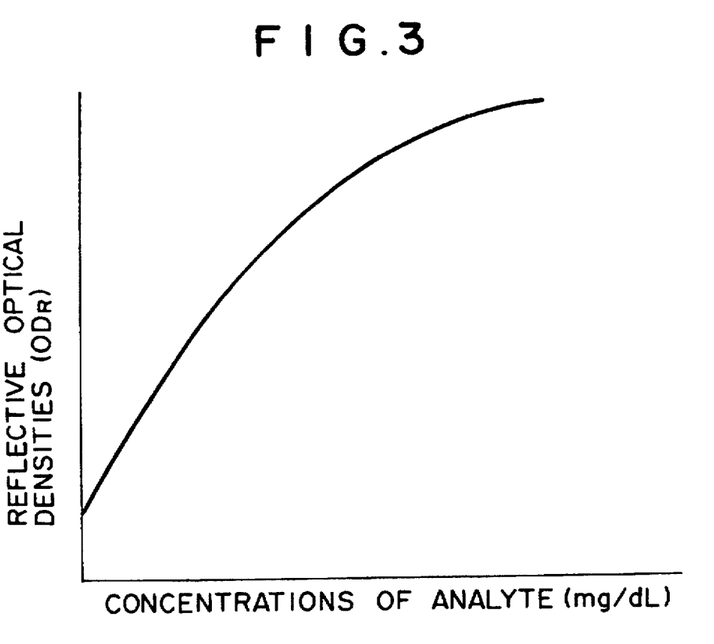
FIG. 3 is a graph showing an example of the standard curve.
Figure 4:
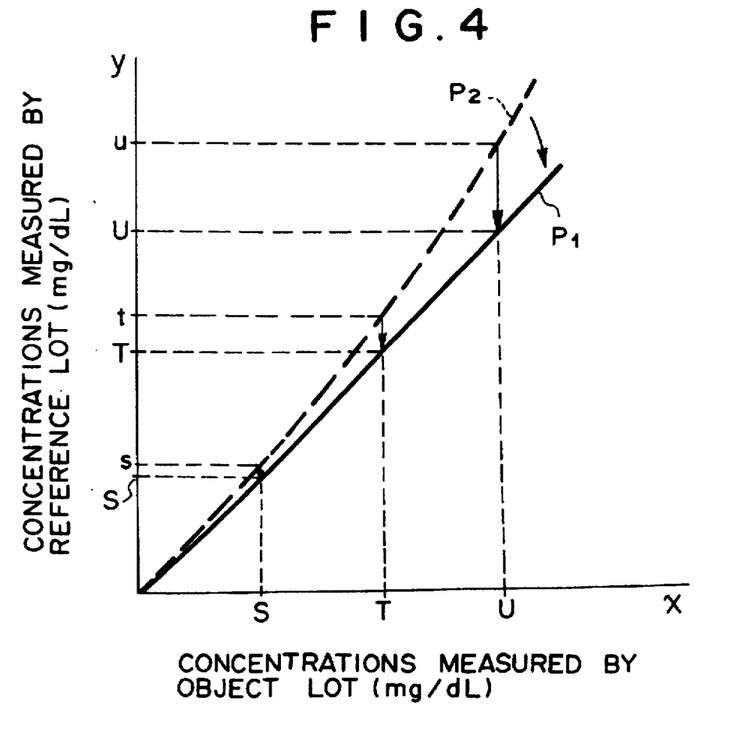
FIG. 4 is a graph for illustrating preparation of the first calibration curve in a method of calibration in accordance with the embodiment.

In this embodiment, fluctuation in the measured concentration due to these factors is compensated for in two steps. That is, a first calibration curve (an example of which is shown in FIG. 4) for compensating for the difference in the properties between the frameless chemical analysis films 1 produced in the reference production lot and those produced in a production lot other than the reference production lot is prepared and a second calibration curve (an example of which is shown in FIG. 1) for compensating for change with time of the chemical analysis films and difference in the biochemical analysis system employed in analysis is prepared. When actually analyzing a specific analyte in a sample liquid on a particular biochemical analysis system, the concentration of the specific analyte in the sample liquid is measured on the particular system and determined according to the standard curve (an example of which is shown in FIG. 3). Then the measured value is corrected according to the first calibration curve and the corrected measured value is further corrected according to the second calibration curve. The value thus obtained is output as a value representing the concentration of the specific analyte in the sample liquid.

Preparation of the standard curve and first and second calibration curves will be described, hereinbelow.

In the maker, reflective optical densities ODR (e.g., $R_H$, $R_M$, $R_L$) of a plurality of (e.g., 3 or 4) standard liquids (e.g., human serum) containing therein a specific analyte in different known concentrations (standard concentrations, e.g., H, M, L) are measured on a reference biochemical analysis system using chemical analysis films 1 of a reference production lot in the same manner as that for quantitative analysis of the specific analyte in a sample liquid. Then the measured values are plotted and a standard curve such as shown in FIG. 3 is obtained. The standard curve is input into a memory such as a floppy disk, a magnetooptic disk, a CD-ROM, an IC card, a ROM or the like (not shown) which is loaded in the reference biochemical analysis system. The standard curve is separately prepared and stored for each analyte.

Then concentrations of three standard liquids containing therein the specific analyte in different three known levels (s, t, u) are measured on the reference biochemical analysis system using chemical analysis films 1 of an object production lot other than the reference production lot in the same manner as that for quantitative analysis of the specific analyte in a sample liquid. Then the measured values (S, T, U) obtained are plotted, thereby obtaining a curve P2 shown in FIG. 4. In order to equalize the measured values obtained by use of the chemical analysis films 1 of the object lot with the measured values obtained by use of the chemical analysis films 1 of the reference lot, a first calibration curve for correcting the curve P2 to a linear line P1 represents by y=x is derived.

That is, when the curve P2 is quadric, (x, y)=(S, s), (T, t), (U, u) is substituted in equation $y=ex^2+dx+c$, and three coefficients e, d, c are determined, whereby the first calibration curve is derived.

The information on the first calibration curve is stored in a magnetic card as magnetic codes, and is supplied to a user (an operator of a biochemical analysis system in medical facilities, laboratories and the like) together with the chemical analysis films 1 of the object production lot.

On the magnetic card, there are recorded fixed information (information which need not be changed by production lot) including the code and name of the analyte to be analyzed by the chemical analysis film 1, the amount of sample liquid to be spotted onto the chemical analysis film 1, the wavelength of the measuring light, the process for operating data on the basis of the measured optical density, the range of quantitative analysis, the range of display, the number of digits of display, the unit of display and the like as well as variable information including the lot number of the frameless chemical analysis films 1, the correction coefficients for deriving the first calibration curve for the production lot and the like.

A mechanically readable medium such as an optically readable card on which information can be stored as optically readable codes such as bar codes, optical characters or optical marks, and an IC card on which information can be stored as nonvolatile electric or electromagnetic codes may be employed in place of the magnetic card.

On the user side, the information stored on the magnetic card is read by a magnetic card reader electrically connected to their biochemical analysis system, whereby the information including the information on the first calibration curve is taken in a memory built in the user's biochemical analysis system.

Then standard liquids (calibrators) containing therein a specific analyte in different two known levels (v, w) related to the standard curve are spotted onto chemical analysis films 1 of a production lot to be actually used in subsequent analysis of sample liquids and concentrations of the standard liquids are measured on the user's biochemical analysis system which has been provided with the information on the first calibration curve. Then the measured values (V, W) obtained are plotted, thereby obtaining a curve Q2 shown in FIG. 1. In order to equalize the measured values obtained by use of the chemical analysis films 1 of the object lot on the user's biochemical analysis system with the measured values obtained by use of the chemical analysis films 1 of the reference lot, a second calibration curve for correcting the curve Q2 to a linear line Q1 represents by y=x is derived.

That is, (x, y)=(V, v), (W, w) is substituted in equation y=gx+f, and two coefficients f and g are determined, whereby the second calibration curve is derived.

The information on the second calibration curve is stored in the memory in the user's biochemical analysis system automatically on the basis of the measured optical densities read by the light measuring head of the measuring means 16 or manually by operation of a control panel or keyboard of the biochemical analysis system, a keyboard of a personal computer for controlling the biochemical analysis system, or the like. On the basis of the information on the second calibration curve, fluctuation of the measured value due to change with time of the chemical analysis films 1 actually used in quantitative analysis of the specific analyte and that depending on the properties of the biochemical analysis system on which the quantitative analysis is carried out can be compensated for.

When the linear line Q2 passes through the origin, the level of the standard liquids may be one since the linear line can be determined when one point other than the origin which the linear line passes through is known.

Depending on the kind of analyte, the second calibration curve cannot be defined by a linear line and in such a case, the levels of the standard liquids should be at least three.

When actually analyzing a sample liquid, the concentration of the analyte is determined according to the standard curve, and the value of the concentration as determined according to the standard curve is corrected according to the first calibration curve and then the value of the concentration as corrected according to the first calibration curve is further corrected according to the second calibration curve. The corrected value of the concentration thus obtained is output as a final measured value of the concentration of the specific analyte in the sample liquid.

The method of calibration of this embodiment is especially advantageous when preparation of the first calibration curve requires relatively large labor and preparation of the second calibration curve requires relatively small labor.

That is, by allotting preparation of the first calibration curve to the maker, load on the user can be lightened and reliability of analysis can be improved.

When fluctuation in the measured concentration due to change with time of the chemical analysis element and that depending on the biochemical analysis system used are negligible, the step of preparing the second calibration curve may be omitted. In such a case, the user has only to input the information stored on the magnetic card into a magnetic card reader electrically connected to their biochemical analysis system and a data bus (or a magnetic card reader built in their biochemical analysis system).

Though in the embodiment described above, frameless chemical analysis films 1 are employed as the chemical analysis elements, other various chemical analysis elements described above may be employed as the chemical analysis elements in place of the frameless chemical analysis films 1.

Examples of the present invention will be described, hereinbelow.

EXAMPLE 1

In this example, the second calibration curve is a quadric. That is, standard liquids of three levels are employed to determine the second calibration curve.

First step

A plurality of frameless chemical analysis films 1 are taken as samples from the top and bottom of a stack of frameless chemical analysis films 1 of an object production lot other than the reference production lot. Four standard liquids including three control serums (low level L, middle level M and high level H) and distilled water were spotted onto the sample frameless chemical analysis films 1 (each of the control serums onto five films 1 and the water onto two films 1) and the concentrations of Ca in the standard liquids were measured.

A quadric regression of the average of the measured concentration of Ca in each standard liquid and the known concentration of Ca in the standard liquid (reference value) was obtained by a least squares method and values of (x, y) were substituted in the aforesaid formula $y=ex^2+dx+c$, thereby determining three coefficients c, d and e.

The reference value, the average of the measured concentrations of Ca in each standard liquid, the values of the coefficients c, d and e thus determined, and corrected value of the average of the measured concentrations of Ca in each standard liquid corrected according to the first calibration curve obtained by substituting the values of the coefficients c, d and e in the above quadric were as shown in the following table 1.

TABLE 1

|  | ref. value (mg/dL) | ave. (mg/dL) | corrected ave. (mg/dL) |
|---|---|---|---|
| $H_2O$ | −0.66 | −0.23 | −0.36 |
| L | 4.25 | 4.28 | 4.24 |
| M | 9.70 | 9.60 | 9.74 |
| H | 16.49 | 16.02 | 16.55 |

$c = -0.123$,
$d = 1.011$,
$e = 1.72 \times 10^{-3}$

In order to prove the performance of the first calibration curve, two control serums containing therein Ca in different known levels (level 1 and level 2 which were different from those of the aforesaid standard liquids) were spotted onto the sample frameless chemical analysis films 1 and the concentrations of Ca in the control serums were measured, and the measured concentrations were corrected according to the first calibration curve. Results were as shown in the following table 2.

TABLE 2

|  | ref. value (mg/dL) | measured value (mg/dL) | corrected value. (mg/dL) |
|---|---|---|---|
| 1 | 9.79 | 9.62 | 9.765 |
| 2 | 12.02 | 11.73 | 11.975 |

Second step

Using frameless chemical analysis films 1 of said object lot and an object biochemical analysis system (FUJI DRI-CHEM manufactured by FUJI PHOTO FILM Japan) other than the reference biochemical analysis system, a second calibration curve for compensating for fluctuation in the measured concentration due to change with time of the chemical analysis element and that depending on the biochemical analysis system used was prepared.

A plurality of frameless chemical analysis films 1 were taken as samples from the top and bottom of a stack of frameless chemical analysis films 1 of the object production lot. Three standard liquids which were three control serums (low level L, middle level M and high level H) were spotted onto the sample frameless chemical analysis films 1 (each of the control serums onto five films 1) and the concentrations of Ca in the standard liquids were measured on the object biochemical analysis system which had been provided with the information on the first calibration curve.

A quadric regression of the average of the measured concentration of Ca in each standard liquid and the known concentration of Ca in the standard liquid (reference value) was obtained by a least squares method and values of (x, y) were substituted in a quadric formula $y=hx^2+gx+f$, thereby determining three coefficients f, g and h.

The reference value, the average of the measured concentrations of Ca in each standard liquid and the values of the coefficients c, d and e thus determined were as shown in the following table 3.

TABLE 3

|   | ref. value (mg/dL) | ave. (mg/dL) |
|---|---|---|
| L | 4.9 | 3.35 |
| M | 9.6 | 8.30 |
| H | 14.4 | 13.36 |

$f = 1.6713$,
$g = 0.96689$,
$h = 0.11435 \times 10^{-2}$

Then a second calibration curve was obtained by substituting the values of the coefficients f, g and h in the above quadric.

In order to prove the performance of the second calibration curve, tow control serums containing therein Ca in different known levels (level 1 and level 2 which are different from those of the aforesaid standard liquids) were spotted onto the sample frameless chemical analysis films 1 and the concentrations of Ca in the control serums were measured on the object biochemical analysis system which had been provided with the information on the first calibration curve, and the measured concentrations (had been corrected according to the first calibration curve) were corrected according to the second calibration curve. Results were as shown in the following table 4.

TABLE 4

|   | ref. value (mg/dL) | measured value (mg/dL) | corrected value. (mg/dL) |
|---|---|---|---|
| 1 | 5.8 | 4.41 | 5.91 |
| 2 | 7.1 | 5.76 | 7.21 |

As can be understood from table 4, the corrected concentrations corrected by the second calibration curve were very close to the respective reference values.

Figure 5:
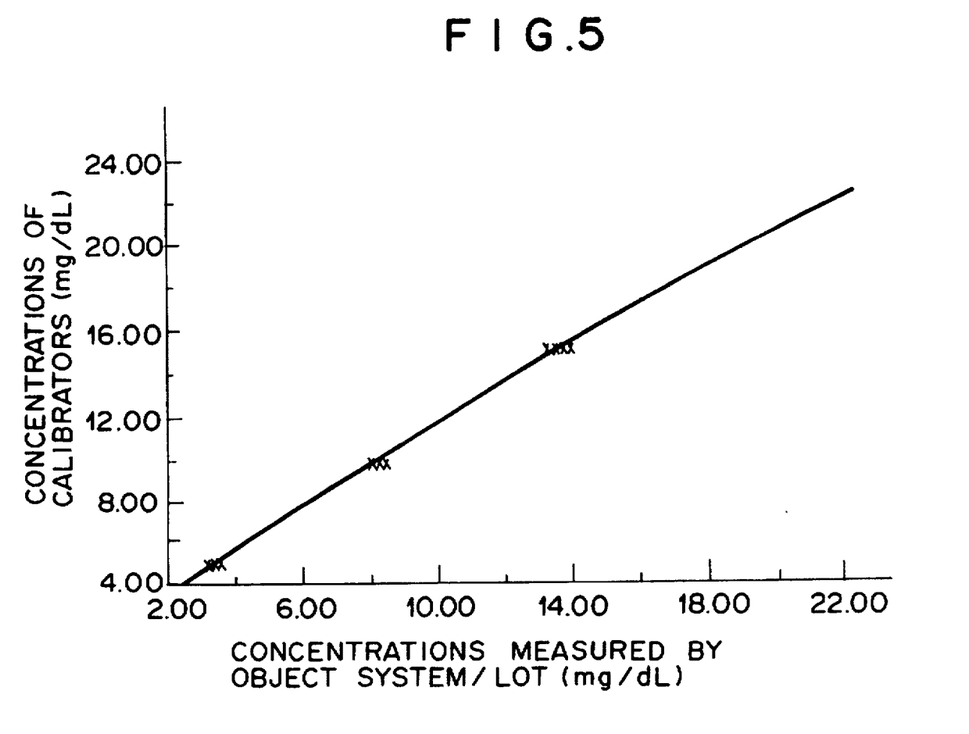
FIG. 5 is a graph showing a second calibration curve obtained in an example.

FIG. 5 shows the second calibration curve obtained in this example.

EXAMPLE 2

In this example, the second calibration curve is a linear line. That is, standard liquids of two levels are employed to determine the second calibration curve.

First step

First step was carried out in the same manner as in the first example.

Second step

Using frameless chemical analysis films 1 of said object lot and an object biochemical analysis system (FUJI DRI-CHEM manufactured by FUJI PHOTO FILM Japan) other than the reference biochemical analysis system, a second calibration curve for compensating for fluctuation in the measured concentration due to change with time of the chemical analysis element and that depending on the biochemical analysis system used was prepared.

A plurality of frameless chemical analysis films 1 were taken as samples from the top and bottom of a pair of stacks of frameless chemical analysis films 1 of the object production lot. One of the stacks was a stack of frameless chemical analysis films 1 just after production and the other was a stack of aged frameless chemical analysis films 1 (had been subjected to a controlled deterioration test, i.e., had been stored at 45° C. for two weeks). The sample frameless chemical analysis films 1 from the former stack will be referred to as "the new sample frameless chemical analysis films 1" and those from the latter stack will be referred to as "the aged sample frameless chemical analysis films 1", hereinbelow. Two standard liquids which were two control serums (low level L, i.e., 5.1 mg/dL, and high level H, i.e., 9.3 mg/dL) were spotted onto the new and aged sample frameless chemical analysis films 1 (each of the control serums onto five films 1) and the concentrations of Ca in the standard liquids were measured on the object biochemical analysis system which had been provided with the information on the first calibration curve.

Coefficients f and g of a linear line y=gx+f were determined by a least squares method for each of the new sample frameless chemical analysis films 1 and the aged sample frameless chemical analysis films 1. The values of the coefficients f and g were as shown in the following table 5.

TABLE 5

|   | f | g |
|---|---|---|
| new sample | −1.60572 | 1.09524 |
| aged sample | −1.67713 | 1.08571 |

The a second calibration curve for each of the new sample frameless chemical analysis films 1 and the aged sample frameless chemical analysis films 1 was obtained by substituting the values of the coefficients f and g in the above linear line.

In order to prove the performance of the second calibration curves, tow control serums containing therein Ca in different known levels (level 1 and level 2 which were different from those of the aforesaid standard liquids) were spotted onto the sample frameless chemical analysis films 1 and the concentrations of Ca in the control serums were measured on the object biochemical analysis system which had been provided with the information on the first calibration curve, and the measured concentrations (had been corrected according to the first calibration curve) were corrected according to the respective second calibration curves. Results were as shown in the following table 6.

TABLE 6

|   |   | ref. value (mg/dL) | measured value (mg/dL) | corrected value. (mg/dL) |
|---|---|---|---|---|
| 1 | new | 6.5 | 5.40 | 6.40 |
|   | aged | 6.5 | 5.36 | 6.48 |
| 2 | new | 8.3 | 7.58 | 8.39 |
|   | aged | 8.3 | 7.44 | 8.40 |

As can be understood from table 6, the corrected concentrations corrected by the second calibration curve were very close to the respective reference values.

What is claimed:

1. In a quantitative analysis of a specific analyte in a sample liquid in which the analyte concentration in the sample liquid is determined on the basis of the optical density of a chemical analysis element spotted with the sample liquid according to a standard curve which is a function representing the relation between the concentration of the specific analyte and the optical density of the chemical analysis element or another physical value corresponding to the optical density which is obtained when the concentration of the specific analyte is measured using a chemical analysis element produced in a first production lot, a method of calibrating the measured concentration of the specific analyte in a sample liquid using a chemical analysis element produced in a second production lot other than the first production lot comprising:

a first step of preparing a first calibration curve in which a plurality of first standard liquids containing therein said specific analyte in different levels which are known are each spotted onto a separate chemical analysis element produced in the second production lot, the concentrations of the specific analyte in the respective first standard liquids are determined according to the standard curve and then there is prepared a first correction calibration curve for correcting the values of the concentrations of the specific analyte in the respective first standard liquids thus determined to the values which would be obtained when the concentrations of the specific analyte in the respective first standard liquids are determined using chemical analysis elements produced in the first production lot and the standard curve, and a second step of preparing a second correction calibration curve in which before quantitatively analyzing the specific analyte in a sample liquid using a chemical element of said second production lot on a particular biochemical analysis system, a plurality of second standard liquids containing therein said specific analyte in different levels which are known are each spotted onto a separate chemical analysis element of the second production lot, the concentrations of the specific analyte in the respective second standard liquids are determined according to the standard curve on said particular biochemical analysis system, the values of the concentrations of the specific analyte in the respective second standard liquids thus determined are corrected according to the first calibration curve, and then there is prepared a second calibration curve for correcting the values of the concentrations of the specific analyte in the respective second standard liquids thus corrected to the values which would be obtained when the concentrations of the specific analyte in the respective standard liquids are determined using chemical analysis elements produced in the first production lot and the standard curve.

2. A method as defined in claim 1 in which said second calibration curve is a linear line passing through the origin and said second standard liquids contains therein said specific analyte in a single level.

3. A method as defined in claim 1 in which said second calibration curve is a linear line and said second standard liquids contains therein said specific analyte in two levels.

4. A method as defined in claim 1 in which said second calibration curve is a quadric or a curve which can be substantially approximated to a quadric and said second standard liquids contains therein said specific analyte in three levels.

5. A method as defined in claim 1 in which information on the calibration curve is stored in a memory and input into said particular biochemical analysis system.

* * * * *